United States Patent
Partridge et al.

(10) Patent No.: US 6,842,648 B2
(45) Date of Patent: Jan. 11, 2005

(54) SYSTEM AND ASSEMBLY HAVING CONDUCTIVE FIXATION FEATURES

(75) Inventors: Scott M. Partridge, Minneapolis, MN (US); Jeffrey T. Bartig, Maplewood, MN (US); Bruce H. KenKnight, Maple Grove, MN (US); Peter T. Kelley, Buffalo, MN (US); Mohan Krishnan, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 163 days.

(21) Appl. No.: 10/054,600

(22) Filed: Jan. 22, 2002

(65) Prior Publication Data

US 2002/0072787 A1 Jun. 13, 2002

Related U.S. Application Data

(62) Division of application No. 09/746,614, filed on Dec. 21, 2000, now Pat. No. 6,574,514, which is a division of application No. 09/349,266, filed on Jul. 7, 1999, now abandoned.

(51) Int. Cl.[7] .............................................. A61N 1/05
(52) U.S. Cl. ...................................... 607/126; 607/122
(58) Field of Search .............................. 607/128, 126, 607/130, 122; 600/375

(56) References Cited

U.S. PATENT DOCUMENTS

| | | | |
|---|---|---|---|
| 3,814,104 A | 6/1974 | Irnich et al. ................. | 128/418 |
| 3,844,292 A | 10/1974 | Bolduc ........................ | 128/418 |
| 4,602,637 A | 7/1986 | Elmqvist et al. ............ | 128/419 |
| 4,662,382 A | 5/1987 | Sluetz et al. ................. | 128/785 |
| 4,716,888 A | 1/1988 | Wesner ........................ | 128/785 |
| 4,763,655 A | 8/1988 | Wirtzfeld et al. ...... | 128/419 PG |
| 5,257,634 A | * 11/1993 | Kroll ........................... | 607/122 |
| 5,305,746 A | 4/1994 | Fendrock .................... | 128/641 |
| 5,324,327 A | 6/1994 | Cohen ......................... | 607/122 |
| 5,476,502 A | * 12/1995 | Rubin ......................... | 607/127 |
| 5,484,435 A | 1/1996 | Fleenor et al. ............... | 606/46 |
| 5,531,779 A | 7/1996 | Dahl et al. .................. | 607/119 |
| 5,772,693 A | 6/1998 | Brownlee .................... | 607/123 |
| 5,782,898 A | 7/1998 | Dahl et al. .................. | 607/119 |
| 5,964,795 A | 10/1999 | McVenes et al. ........... | 607/122 |
| 6,006,139 A | 12/1999 | Kruse et al. ................. | 607/125 |
| 6,083,247 A | 7/2000 | Rutten et al. .................. | 607/9 |
| 6,148,238 A | * 11/2000 | Rutten ........................ | 607/126 |
| 6,256,541 B1 | * 7/2001 | Heil et al. ................... | 607/122 |

FOREIGN PATENT DOCUMENTS

| | | | |
|---|---|---|---|
| EP | 0706807 | 9/1995 | ............ A61N/1/05 |
| WO | 96/15665 | 5/1996 | ............ A01N/1/05 |
| WO | 99/15229 | 4/1999 | ............ A61N/1/05 |
| WO | 99/15230 | 4/1999 | ............ A61N/1/05 |

* cited by examiner

Primary Examiner—George R. Evanisko
(74) Attorney, Agent, or Firm—Schwegman, Lundberg, Woessner & Kluth, P.A.

(57) ABSTRACT

A lead having a distal end electrode assembly adapted for implantation on or about the heart or within a vein and for connection to a system for monitoring or stimulating cardiac activity. The electrode assembly includes conductive fixation features, such as conductive tines or flexible members, in combination with non-conductive fixation features. The conductive fixation features also include tines coated with a conductive material. The fixation features further include conductive tines which are retractable. A defibrillation coil is optionally disposed at the distal end of the lead in combination with the conductive tines.

17 Claims, 12 Drawing Sheets

SYSTEM AND ASSEMBLY HAVING CONDUCTIVE FIXATION FEATURES

CROSS-REFERENCE TO RELATED APPLICATION(S)

This application is a division of U.S. patent application Ser. No. 09/746,614, filed on Dec. 21, 2000, now U.S. Pat. No. 6,574,514 which is a division of U.S. patent application Ser. No. 09/349,266, filed on Jul. 7, 1999, now abandoned, the specifications of which are incorporated by reference herein.

FIELD OF THE INVENTION

The present invention relates generally to leads for conducting electrical signals to and from the heart. More particularly, it pertains to an electrode having conductive fixation features for delivering electrical charges to and from the heart.

BACKGROUND OF THE INVENTION

Cardiac rhythm systems are used for treating an irregular or unstable heart. The systems include, among other things, pacemakers which deliver timed sequences of low electrical energy to the heart, such as via a lead having one or more electrodes. Leads have been implanted in the body for electrical cardioversion or pacing of the heart. More specifically, electrodes implanted in or about the heart have been used to reverse (i.e., defibrillate or cardiovert) or sense certain life threatening arrhythmias, or to stimulate contraction (pacing) of the heart, where electrical energy is applied to the heart via the electrodes to return the heart to normal rhythm.

Cardiac pacing and/or sensing may be performed by the transvenous method or by electrodes implanted directly onto the epicardium. Traditionally, to attach a lead epicardially, a thoracotomy is performed where the thorax is opened to obtain access to the heart. This procedure involves painful and expensive surgery for the patient. Transvenous pacing may be temporary or permanent. In temporary transvenous pacing an electrode catheter is introduced into a peripheral vein and fluoroscopically positioned against the endocardium.

Traditional permanent transvenous pacing is performed under sterile surgical conditions where an electrode is positioned in the ventricle or atrium through a subclavian vein, and the proximal terminals are attached to a pulse generator which is implanted subcutaneously. The distal tip of the lead is positioned within an apex of the heart to hold the lead in place. Leads which are implanted in the apex of the heart have a backstop, which assists in preventing the lead from floating, and allows for the distal end of the lead to become fixated therein. Potential complications induced by the presence of the lead within the chambers of the heart, however, can preclude lead implantation of the lead within the chambers of the heart.

One approach to resolve this issue is to implant the lead transvenously. When a lead is implanted transvenously, the passage has no termination into which the lead can be positioned, resulting in a floating lead. One of the drawbacks of a floating lead is that the performance of the electrical interface between the electrode and the tissue can be diminished. In addition, the veins or arteries are filled with blood, surrounding the electrode, which further inhibits the electrical interface between the electrode and the tissue.

Defibrillation, which is used to treat a heart which is beating too quickly, delivers a high energy electrical stimulus which allows the heart to reestablish a normal rhythm. In addition to a defibrillating electrode can be combined with a pacing and/or sensing electrode. To obtain lower pacing and sensing thresholds, the pacing/sensing electrode is traditionally disposed at the tip of the lead, which is positioned deep within an apex of the heart at the largest center of mass of the heart. To minimize sensing problems following a shock from the defibrillating electrode, the defibrillating electrode is separated away from the sensing/pacing electrode on the lead. As the defibrillating electrode is moved away from the tip of the lead, however, the shock strength requirement increases resulting in increased demands on the battery of the cardiac rhythm system.

Accordingly, there is a need for an implantable lead that is capable of placement and fixation in other regions of the heart, such as within vascular structures. In addition, there is a need for a lead having an electrode for positioning within a passage, such as a vein or artery, that allows for fixation of the lead. There is also a need for a body implantable lead which allows for effective stimulation from a defibrillation electrode. There is further a need for a lead that is capable of effectively defibrillating the heart, and also pacing/sensing the heart in a limited area.

SUMMARY OF THE INVENTION

The present invention relates to a lead assembly having a lead body extending from a distal end to a proximal end, and includes a conductor. The lead assembly further includes an electrode assembly of at least one electrode, and the electrode assembly is electrically coupled with the conductor. The electrode assembly has an electrically conductive tine adapted for fixating the lead assembly within tissue. In one embodiment, the tine has a first end coupled with the lead body and a second end which extends away from the lead body.

In another embodiment, the tine is formed of an electrically conductive material, for instance, conductive silicone. In another embodiment, the conductive tine includes a conductive coating. In yet another embodiment, the conductive tine is molded to the conductor. The conductive tine further optionally includes one or more non-conductive tines adapted for fixating a portion of the lead assembly. In addition, a defibrillation electrode is disposed at the distal end of the lead body in another embodiment.

In one embodiment, the lead assembly, which has a lead body extending from a distal end to a proximal end, includes a conductor. The lead assembly further includes an electrode assembly of at least one electrode, and the electrode assembly is electrically coupled with the conductor. The electrode assembly has an electrically conductive cone adapted for fixating the lead assembly within tissue. In one embodiment, the cone includes a conductive ring disposed on a distal end of the cone.

In another embodiment, a lead assembly has a lead body extending from a distal end to a proximal end, and includes a conductor. The lead assembly further includes an electrode assembly of at least one electrode, and the electrode assembly is electrically coupled with the conductor. The electrode assembly has an electrically conductive tine adapted for fixating the lead assembly within tissue. A conductive member is disposed within a portion of the conductive tine and is electrically coupled with the electrode assembly.

In one embodiment, the conductive tine includes a partial coating of non-conductive material. In another embodiment, a plurality of conductive tines are provided. The conductive member, in one embodiment, is a wire. In another embodiment, the conductive member is a flat wire or a foil. In yet another embodiment, the conductive tine extends from a first end proximate to the lead body to a second end disposed away from the lead body, and a conductive cap is at the second end of the conductive tine.

In another embodiment, a lead assembly is disclosed which has a lead body extending from a distal end to a proximal end, and includes a conductor. An intermediate portion of the lead body has a straight lead body. The lead assembly further includes a conductive fixation feature which extends away from the lead body. The conductive fixation feature is a protrusion which extends from the intermediate portion of the lead body, and includes an electrode. In one embodiment, the electrode is a sensing or pacing electrode. In another embodiment, the conductive fixation feature is a conductive tine. In addition, the tine includes a cap coupled with the tine in another embodiment. In yet another embodiment, a non-conductive tine is coupled with the lead body and is adapted for fixating a portion of the lead assembly within tissue.

In yet another embodiment, a lead assembly has a lead body extending from a distal end to a proximal end, and includes a conductor. A defibrillation electrode is electrically coupled with the conductor, and is disposed at a second end of the conductor forming a defibrillation tip at the distal end of the lead body. The lead assembly further includes, in another embodiment, a second defibrillation coil disposed at an intermediate portion of the lead body. In addition, the lead assembly includes an electrically conductive tine coupled with a portion of the lead body, in one embodiment. The conductive tine optionally has a first end coupled with the lead body and a second end which extends away from the lead body. In another embodiment, the conductive tine is partially covered with non-conductive material. A conductive bead, in one embodiment, is coupled with a distal end of the conductive tine. In another embodiment, the tine is electrically common with the defibrillation electrode. An electrical discharge surface, in a further embodiment, is disposed between the second defibrillation coil and the distal defibrillation tip, where insulation is optionally disposed between the conductive tine and the defibrillation coil.

A lead assembly, in another embodiment, has a lead body extending from a distal end to a proximal end, and includes a conductor. The lead assembly further includes an electrode assembly of at least one electrode, and the electrode assembly is electrically coupled with the conductor. The electrode assembly has a plurality of electrically conductive tines adapted for fixating the lead assembly within tissue, and the conductive tines are retractable. In one embodiment, the tines have a first end extending from a hinge point and a second end which extends away from the hinge point, where the conductive tine flex at the hinge point. In a retracted position, the retractable tines are disposed in a lumen of the lead body. In an extended position, the retractable tines are extended out of the lumen.

In another embodiment, a lead assembly has a lead body extending from a distal end to a proximal end, and includes a conductor. The lead assembly further includes an electrically conductive fitting coupled with the conductor. An electrode assembly is coupled with the fitting. The electrode assembly including an electrically conductive tine is adapted for fixating the lead assembly within tissue and is molded to the fitting. In one embodiment, the tine is formed of a conductive polymer. In another embodiment, the tine is formed of a conductive rubber or elastomer.

In yet another embodiment, a lead assembly has a lead body extending from a distal end to a proximal end, and includes a conductor. The lead assembly further includes an electrode assembly of at least one electrode, and the electrode assembly is electrically coupled with the conductor. The electrode assembly has a conductive fixation feature which is adapted to send and receive electrical signals. The conductive fixation feature extends from a first end to a second end and includes a flexible and conductive intermediate portion between the first end and the second end. The intermediate portion is flexible away from the conductor. In one embodiment, the first end of the conductive fixation feature is coupled with the lead body and the second end is movably coupled with the lead body. The lead assembly further includes, in another embodiment, a locking mechanism adapted to maintain the intermediate portion in a flexed position. In another embodiment, the locking mechanism includes a slider movably disposed within a slot, and an interference slot sized to engage the slider. The slider is coupled with the second end of the conductive fixation feature. The lead assembly further includes a deployment mechanism, in another embodiment. Examples of deployment mechanisms include a wire or a balloon catheter.

Another embodiment is a lead assembly which has a lead body extending from a distal end to a proximal end, and includes a conductor. The lead assembly further includes an electrode assembly of at least one electrode, and the electrode assembly is electrically coupled with the conductor. A sheath of conductive material is disposed over the electrode assembly. The sheath, in one embodiment, is formed of a conductive polymer. In another embodiment, the sheath is formed of a conductive urethane. In one embodiment, the electrode assembly comprises a defibrillation coil.

In yet another embodiment, a system for delivering signals to the heart includes an electronics system including a cardiac activity sensor and a signal generator for producing signals to stimulate the heart, and a lead assembly. The lead assembly has a lead body extending from a distal end to a proximal end, and includes a conductor. The lead assembly further includes an electrode assembly of at least one electrode, and the electrode assembly is electrically coupled with the conductor. The electrode assembly has an electrically conductive tine adapted for fixating the lead assembly within tissue. The tine has a first end coupled with the lead body and a second end which extends away from the lead body. In one embodiment, the tine is formed of a conductive polymer. In another embodiment, the tine is formed of a conductive polymer, rubber, or elastomer. The conductive tine, in one embodiment, includes a conductive coating. In yet another embodiment, the conductive tine is molded to the conductor. The conductive tine further optionally includes one or more non-conductive tines adapted for fixating a portion of the lead assembly. In yet another embodiment, the conductive tine is a wire extending away from the lead body.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims and their equivalents.

Figure 1:
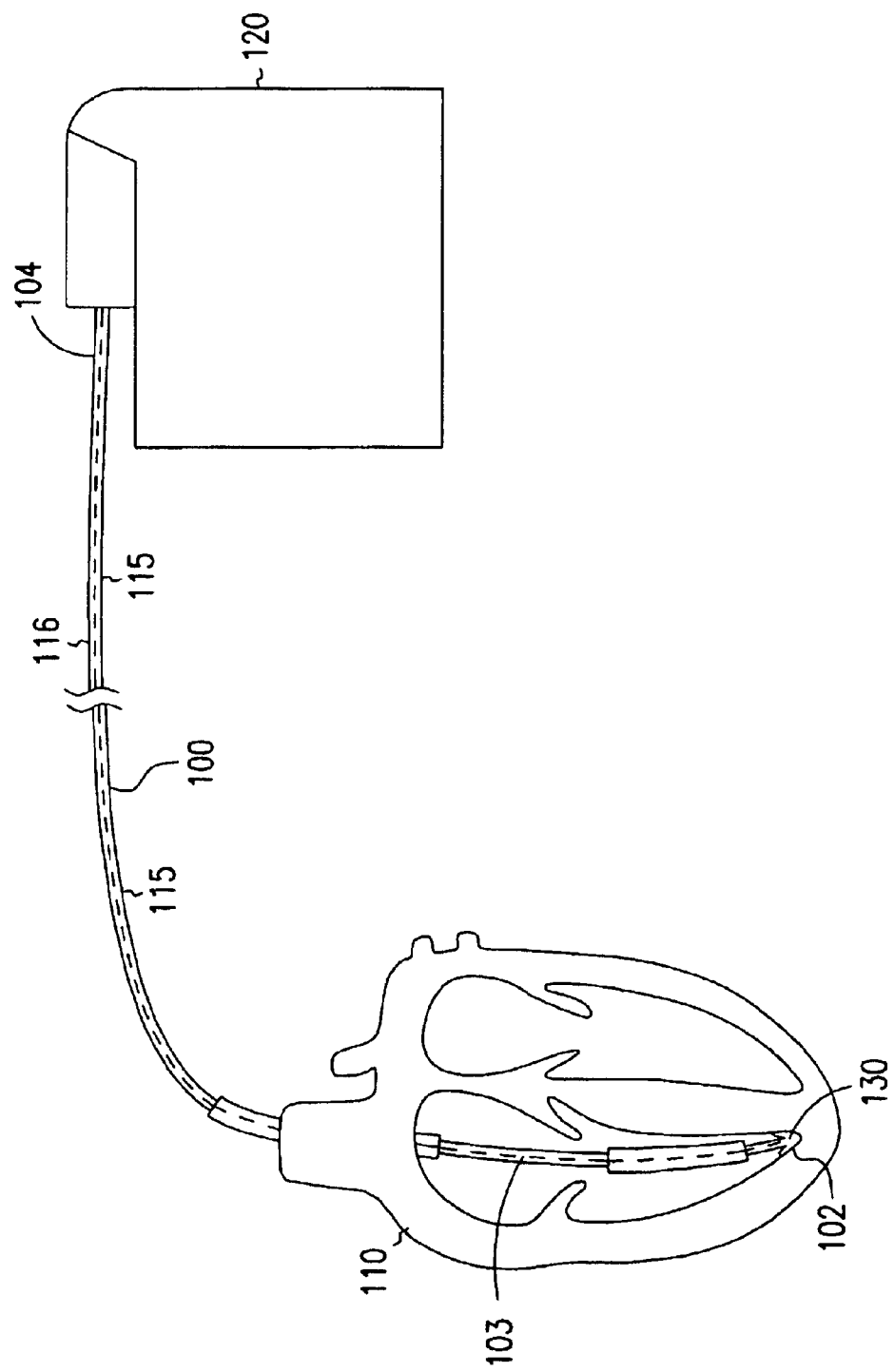
FIG. 1 illustrates a system for monitoring and stimulating the heart constructed in accordance with one embodiment.

FIG. 1 illustrates a lead 100 for delivering electrical pulses to stimulate the heart 110 and/or for receiving electrical pulses to monitor the heart 110. The lead 100 has a distal end 102 adapted for connection within a patient and a proximal end 104. The proximal end 104 has a terminal connector which electrically connects the various electrodes and conductors within the lead body to a pulse generator 120 and signal sensor. The terminal connector provides for the electrical connection between the lead 100 and the pulse generator 120. The pulse sensor and generator 120 contains electronics to sense various electrical signals of the heart 110 and also produce current pulses for delivery to the heart 110. The pulse sensor and generator 120 also contains electronics and software necessary to detect certain types of arrhythmias and to correct for them.

The lead 100 includes a lead body 115, an elongate conductor 116 contained within the lead body 115, and at least one electrode assembly 130. In one embodiment, the electrode assembly 130 is disposed proximate to the distal end 102 of the lead 100. In another embodiment, the electrode assembly 130 is disposed between the distal end 102 and the proximal end 104 of the lead 100, at an intermediate portion 103 of the lead 100. The lead body 115 is covered by a biocompatible insulating material. Silicone rubber or other insulating material is used for covering the lead body 115.

The conductor 116 comprises, in one embodiment, a coil. A conductor coil is capable of withstanding constant, rapidly repeated flexing. The coiled construction is wound relatively tightly providing a maximum number of conductor turns per unit length, which allows for strain distribution. The spirally coiled spring construction of the conductor also permits a substantial degree of elongation, within the elastic limits of the material, as well as distribution along the conductor of flexing stresses which otherwise might be concentrated at a particular point.

The elongate conductor 116 defines a lumen therein and thereby is adapted to receive a stiffening stylet that extends through the length of the lead 100. The stylet stiffens the lead 100, and can be manipulated to introduce an appropriate curvature to the lead 100. The manipulation of the stylet facilitates the insertion of the lead 100 into and through a vein and through an intracardiac valve to advance the distal end 102 of the lead 100 into, for example, the right ventricle of the heart. A stylet knob is coupled with the stylet for rotating the stylet, advancing the conductor into tissue of the heart, and for manipulating the lead 100.

Figure 2:
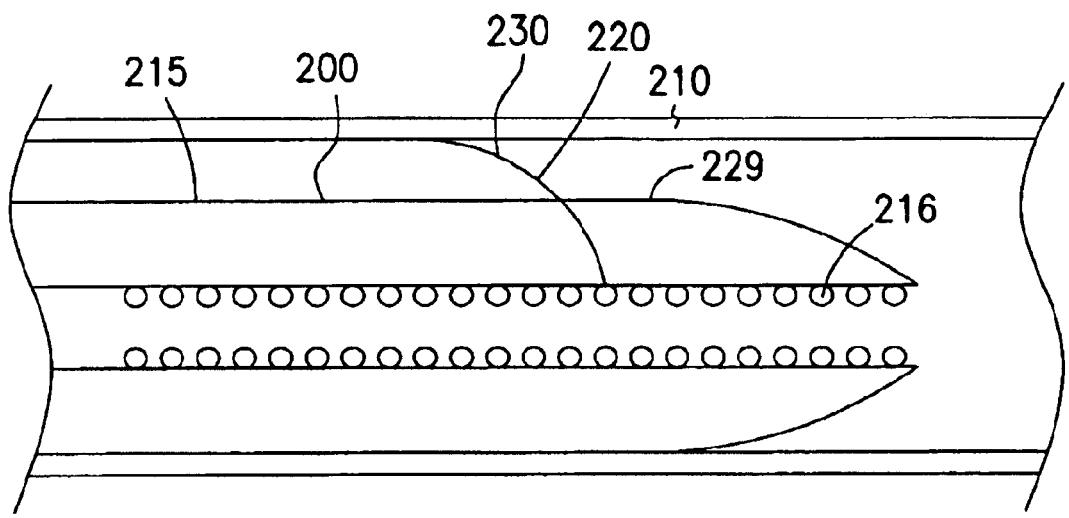
FIG. 2 is a cross-section of an electrode assembly constructed in accordance with one embodiment.

The electrode assembly 130 is adapted to be coupled with tissue of a patient, for example, within a heart 110 or in a vein 210, as illustrated in FIG. 2. In one embodiment, an electrode assembly 230 includes at least one electrically conductive tine 220 which is coupled with a lead 200. The tine 220 is, in one embodiment, disposed through a lead body 215 and is coupled with a conductor 216, as further discussed below. The tine 220 is adapted to send and receive electrical signals within a patient, serving as an electrode, and also assists in fixating the lead 200 within a patient. The tine 220, in one embodiment, comprises a slender projection which projects from the lead body 215 at an angle of less than 90 degrees. In another embodiment, the tine 220 is disposed substantially traverse to the lead body 215 prior to and/or during installation within, for instance, a vein or an artery. In one embodiment, the tine 220 comprises an angled projection disposed on a straight portion 229 of the lead body 215.

The tine 220 comprises a conductive element formed of a conductive material, for example, a metal wire. Alternatively, in another embodiment, the tine 220 is formed of a flat wire or a foil. The tine 220 is electrically coupled with a conductor coil 216, for instance, by welding. In addition, the tine 220 is coupled with tissue or within the wall of the vein 210 such that the tine 220 can send and receive signals to and from the pulse sensor and generator. The tine 220 is adapted to sense and/or pace when the lead 200 is implanted into a patient. In another embodiment, the tine 220 is formed of a semi-rigid material, such as wire, and assists in fixating the lead 200 within tissue, for example, a vein 210.

Figure 3:
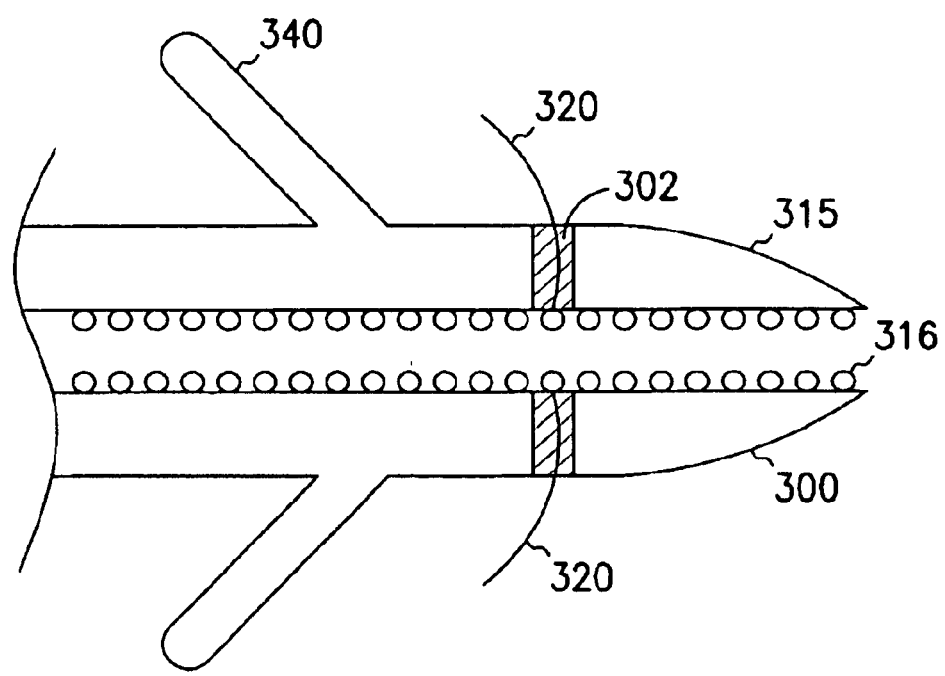
FIG. 3 is a cross-section of an electrode assembly constructed in accordance with one embodiment.

FIG. 3 illustrates another embodiment of a lead 300. The lead 300 includes a plurality of electrically conductive tines 320 which are coupled with the lead 300. In one embodiment, the conductive tines 320 are electrically coupled with a conductor 316, and are adapted to send and receive electrical signals within a patient, as discussed in the embodiment illustrated in FIG. 2. In this embodiment, the conductive tines 320 function as an electrode. In another embodiment, the conductive tines 320 are coupled with an electrode 302 which is disposed on the lead body 315, such as a ring electrode. The conductive tines 320 and the electrode 302 work together to send and receive electrical signals within a patient. The conductive tines 320, in yet another embodiment, comprise slender projections which project from the lead body 315.

The conductive tines 320 comprise conductive elements formed of a conductive material, for example, metal wires. Alternatively, in another embodiment, the conductive tines 320 are formed of flat wires or foils. The conductive tines 320 are electrically coupled with conductor coil 316, for instance, by welding. The conductive tines 320 are also coupled with tissue or within the wall of the vein to facilitate sending and receiving signals between the patient and the pulse sensor and generator.

In another embodiment, the lead 300 also includes non-conductive tines 340. The non-conductive tines 340 are formed of a non-conductive material, for example, a polymer. The non-conductive tines 340 are coupled with the lead body 315 and further assist in fixating the lead 300 within a heart, a vein, or other location within a patient. In one embodiment, the non-conductive tines 340 comprise slender projections which extend away from the lead body 315, for instance, at an angle. In another embodiment, the tines 340 are conductive.

Figure 4A:
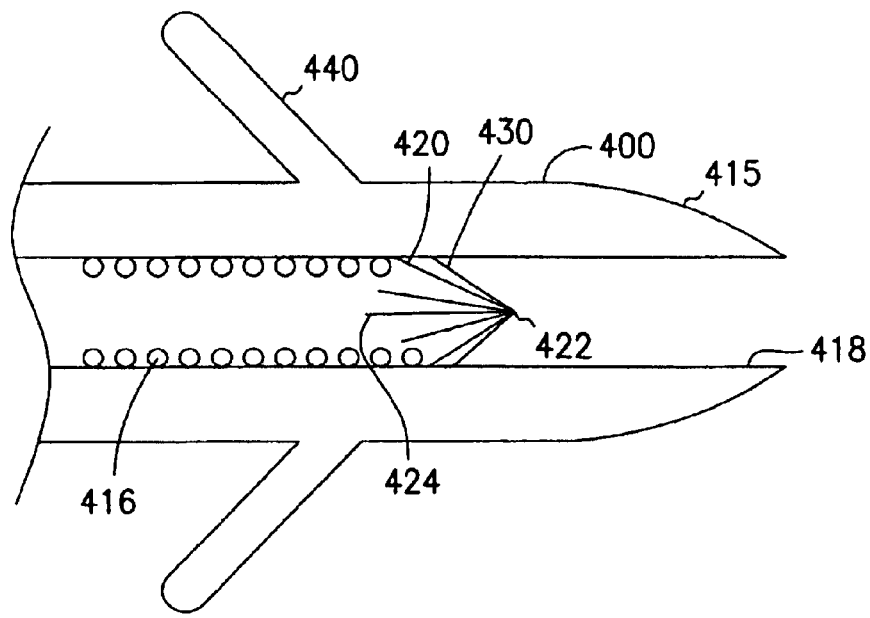
FIG. 4A is a cross-section of an electrode assembly constructed in accordance with one embodiment.
Figure 4B:
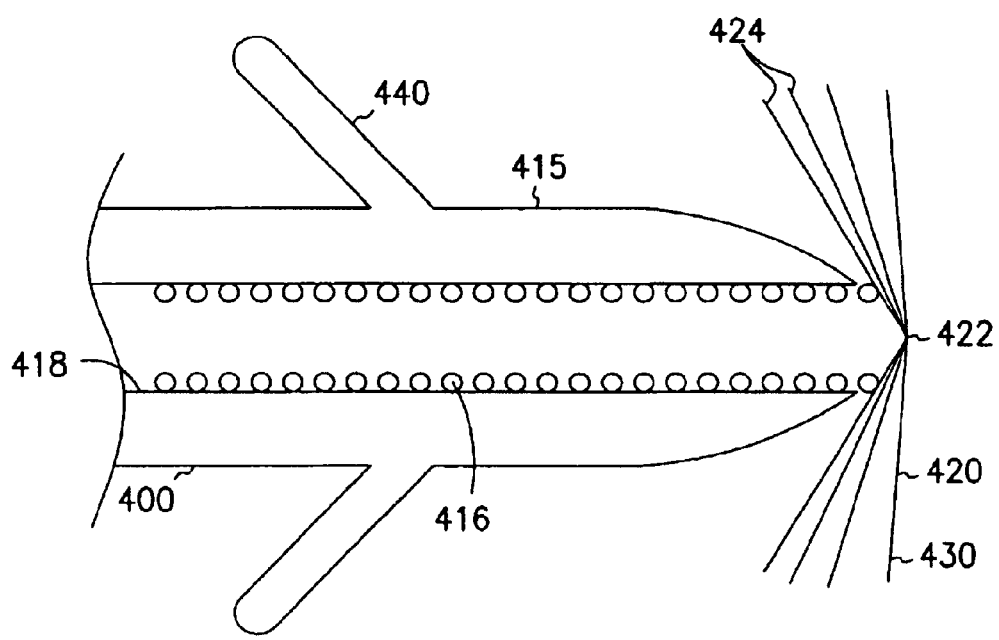
FIG. 4B is a cross-section of an electrode assembly constructed in accordance with one embodiment.

FIGS. 4A and 4B illustrate yet another embodiment of a lead 400. In one embodiment, an electrode assembly 430 includes a plurality of conductive tines 420, or optionally a single conductive tine, which are coupled with a lead 400. The conductive tines 420 are coupled with a conductor 416, as further discussed below. The conductive tines 420 are adapted to send and receive electrical signals within a patient, serving as an electrode, and also assists in fixating the lead 400 within a patient. The conductive tines 420 are adapted to sense and/or pace when the lead 400 is implanted into a patient.

The conductive tines 420 comprise conductive elements formed of a conductive material, for example, a metal wire. Alternatively, in another embodiment, the conductive tines 420 are formed of a flat wire or a foil. In another embodiment, the tines 420 is formed of a semi-rigid material, such as wire, and assists in fixating the lead 400 within tissue, for example, a vein. The conductive tines 420 are electrically coupled with a conductor coil 416, for instance, by welding. In addition, the conductive tines 420 extend from a hinge point 422 to a distal end 424 for each tine. The conductor 416 is coupled with the conductive tines 420 proximate to the hinge point 422, and the conductive tines 420 are adapted to flex at the hinge point 422.

During implant of the lead 400 or when the conductive tines 420 are not in use, the conductive tines 420 are retracted toward the conductor coil 416. The retracted conductive tines 420 are disposed within a lumen 418 of the lead 400 in a recessed position, as shown in FIG. 4A. The conductive tines 420, when disposed within the lead 400, are spring-loaded such that the tines 420 expand away from the conductor coil 416 when the conductive tines 420 are outside of the lead 400. To install the conductive tines 420 from the recessed position of FIG. 4A, force is exerted on the conductor coil 416 to push the retracted conductive tines 420 out of the lead 400. Alternatively, other mechanisms, such as a stylet, are used to extend the conductive tines 420 from the recessed position.

When the conductive tines 420 are extended out of lumen 418 of the lead 400, as shown in FIG. 4B, the conductive tines 420 expand away from the conductor coil 416, for example, by the force of a spring. After the conductive tines 420 are expanded, the conductive tines 420 are in position to engage with tissue, such as within a vein. The conductor tines 420 are expandable and retractable, which allows for the tines 420 to be used in conjunction with, or in alternative to, other electrodes, providing increased flexibility before or after the lead 400 has been implanted into a patient.

In another embodiment, the lead 400 also includes non-conductive tines 440. The non-conductive tines 440 are formed of a non-conductive material, for example, a polymer. The non-conductive tines 440 are coupled with the lead body 415 and further assist in fixating the lead 400 within a heart, a vein, or other location within a patient. In one embodiment, the non-conductive tines 440 comprise slender projections which extend away from the lead body 415, for instance, at an angle.

Figure 5:
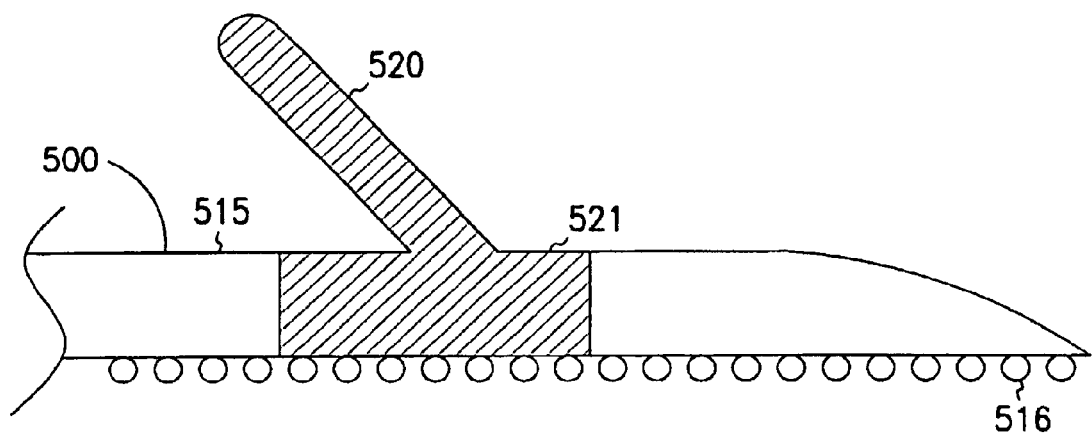
FIG. 5 is a cross-section of an electrode assembly constructed in accordance with one embodiment.

FIG. 5 illustrates another embodiment of a lead 500, which includes at least one electrically conductive tine 520 coupled with the lead 500, and is electrically coupled with a conductor coil 516. The conductive tine 520 is adapted to send and receive electrical signals within a patient such that the conductive tine 520 serves as an electrode. The conductive tine 520 also assists in fixating the lead 500 within a patient, for instance, within a vein. The conductive tine 520, in one embodiment, comprises a slender projection which projects from the lead body 515.

The conductive tine 520, in one embodiment, is molded directly to the conductor coil 516, and is electrically coupled thereto. In one embodiment, the conductive tine 520 forms a portion 521 of the lead body 515, which increases the sensing and/or pacing area of the conductive tine 520. Alternatively, in another embodiment, the conductive tine 520 is formed as a separate component, and is coupled with the conductor coil 516 and the lead body 515. The lead body 515 is formed of non-conductive material and insulates the conductive tine 520 which is molded on to, or otherwise formed on or within the lead body 515. In another embodiment, the conductive tine 520 is formed of a conductive material, for example, using a conductive polymer. Suitable materials for molding or otherwise forming the conductive tine 520 include, but are not limited to: conductive polymers, rubbers, or elastomers like conductive silicone rubber and conductive thermoplastic elastomers like polyurethane elastomers, polyether-ester elastomers, and polyether-amide elastomers. As mentioned above, the conductive tine 520 is electrically coupled with the conductor coil 516. In addition, the tine 520 is coupled with tissue or within the wall of a vein such that the tine 520 can send and receive signals to and from the pulse sensor and generator.

Figure 6:
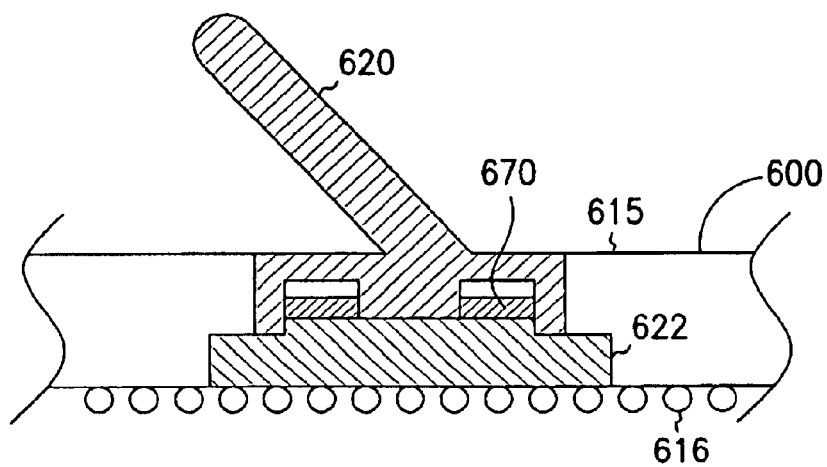
FIG. 6 is a cross-section of an electrode assembly constructed in accordance with one embodiment.

In another embodiment, as illustrated in FIG. 6, a lead 600 includes at least one electrically conductive tine 620, which is coupled with the lead 600 and electrically coupled with a conductor coil 616 of the lead 600. The conductive tine 620 is adapted to send and receive electrical signals within a patient, such that the conductive tine 620 serves as an electrode. The conductive tine 620 also assists in fixating the lead 600 within a patient, for instance, within a vein. The conductive tine 620, in one embodiment, comprises a slender projection which projects from the lead body 615.

A fitting 622 is electrically coupled with the conductor coil 616, for instance, by welding the fitting 622 to the conductor coil 616. Alternatively, the fitting 622 is electrically coupled with the conductor coil 616 using conductive adhesive. The fitting 622 is formed from a conductive material, such as stainless steel or other conductive metals. The conductive tine 620, in one embodiment, is molded to the fitting 622, and is electrically coupled thereto. Alternatively, in another embodiment, the conductive tine 620 is formed as a separate component, and is coupled with the fitting 622 and the lead body 615. In one embodiment, the fitting 622 includes a series of holes 670 which are formed through the fitting 622. The holes 670 allow for the conductive material forming the conductive tine 620 to therethrough, thereby allowing for attachment of the conductive tine 620 to the fitting 622.

The lead body 615 is formed of non-conductive material and insulates a portion of the conductive tine 620 which is molded on to, or otherwise formed on or within the lead body 615. In another embodiment, the conductive tine 620 is formed of a conductive material, for example, using a conductive polymer. In yet another embodiment, the conductive tine 620 is formed of a flexible material. Suitable materials for molding or otherwise forming the conductive tine 620 include, but are not limited to: conductive polymers, rubbers, or elastomers like conductive silicone rubber and conductive thermoplastic elastomers like polyurethane elastomers, polyether-ester elastomers, and polyether-amide elastomers. As mentioned above, the conductive tine 620 is electrically coupled with the fitting 622 and the conductor coil 616. In addition, the tine 620 is coupled with tissue or within the wall of a vein such that the tine 620 can send and receive signals to and from the pulse sensor and generator.

Figure 7:
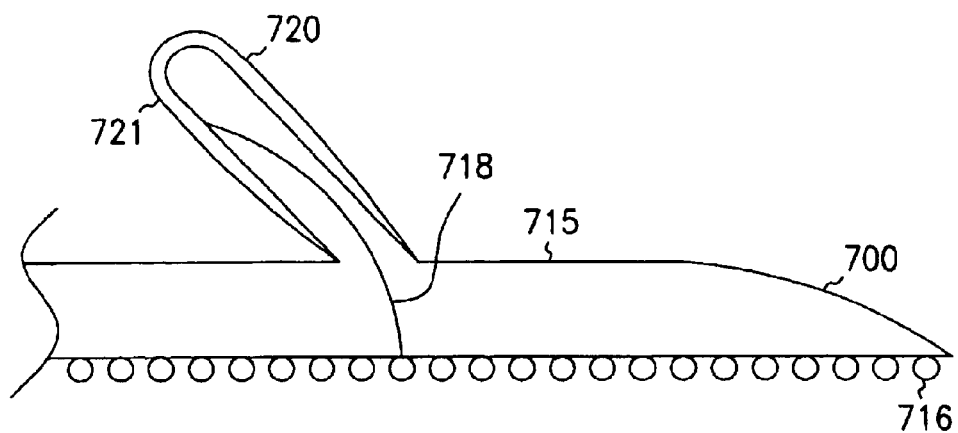
FIG. 7 is a cross-section of an electrode assembly constructed in accordance with one embodiment.

FIG. 7 illustrates yet another embodiment of a lead 700 which includes at least one conductive tine 720. The conductive tine 720 is coupled with the lead 700 and electrically coupled with a conductor coil 716. The conductive tine 720 is adapted to send and receive electrical signals within a patient, the conductive tine 720 serving as an electrode, or supplementing another electrode. The conductive tine 720 also assists in fixating the lead 700 within a patient, for instance, within a vein. The conductive tine 720, in one embodiment, comprises a slender projection which projects from the lead body 715. After implanting the lead 700, the conductive tine 720 assists in mechanically fixating the lead 700 within tissue.

The conductive tine 720, in one embodiment, is molded to or within the lead body 715, and is coated with a conductive coating 721. The conductive coating 721 is electrically coupled with the conductor coil 716, for instance by a wire 718 or another conductive element. Suitable materials for the conductive coating 721 include, but are not limited to: conductive polymers, rubbers, or elastomers like conductive silicone rubber and conductive thermoplastic elastomers like polyurethane elastomers, polyether-ester elastomers, and polyether-amide elastomers. The lead body 715 is formed of non-conductive material and insulates the conductive tine 720 and also the conductor coil 716.

Figure 8A:
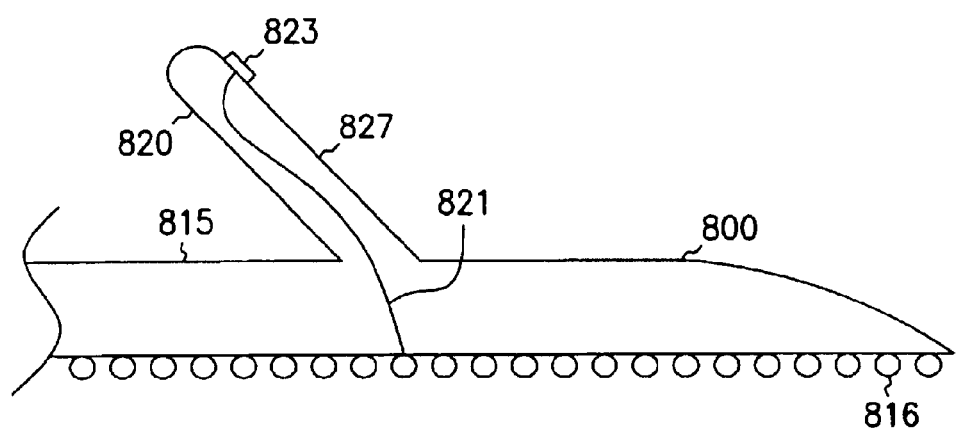
FIG. 8A is a cross-section of an electrode assembly constructed in accordance with one embodiment.
Figure 8B:
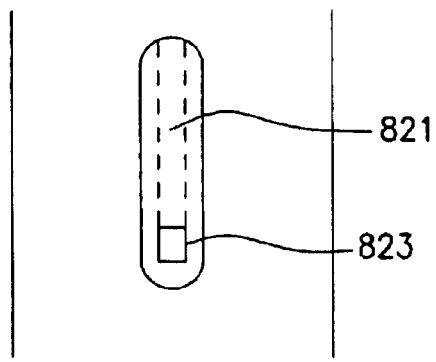
FIG. 8B is a side elevational view of the electrode assembly shown in FIG. 8A.

In another embodiment, a lead 800 is provided with at least one conductive tine 820, as illustrated in FIGS. 8A and 8B. The tine 820 is, in one embodiment, coupled with a lead body 815 and is electrically coupled with a conductor coil 816, as further discussed below. The tine 820 is adapted to send and receive electrical signals within a patient, serving as an electrode, or supplements the pacing or sensing of another electrode. In addition, the conductive tine 820 assists in fixating the lead 800 within a patient.

The tine 820, in one embodiment, comprises a slender projection which projects from the lead body 815 at an angle. The tine 820 includes non-conductive material 827, and an exposed portion as further discussed below. Disposed within the tine 820 is a conductive element 821 formed of a conductive material, for example, a metal wire. Alternatively, in another embodiment, the conductive element 821 is formed of a flat wire or a foil. The conductive element 821 is electrically coupled with a conductor coil 816, for instance, by welding or by conductive adhesive. The non-conductive material 827 partially covers the conductive element 821. A portion 823 of the conductive element 821 is exposed, allowing for the portion 823 to be exposed to tissue. Referring to FIG. 8B, the portion 823 which is exposed can be in a variety of shapes and sizes. In one embodiment, the exposed portion 823 of the conductive element 821 is square shaped.

Figure 9:
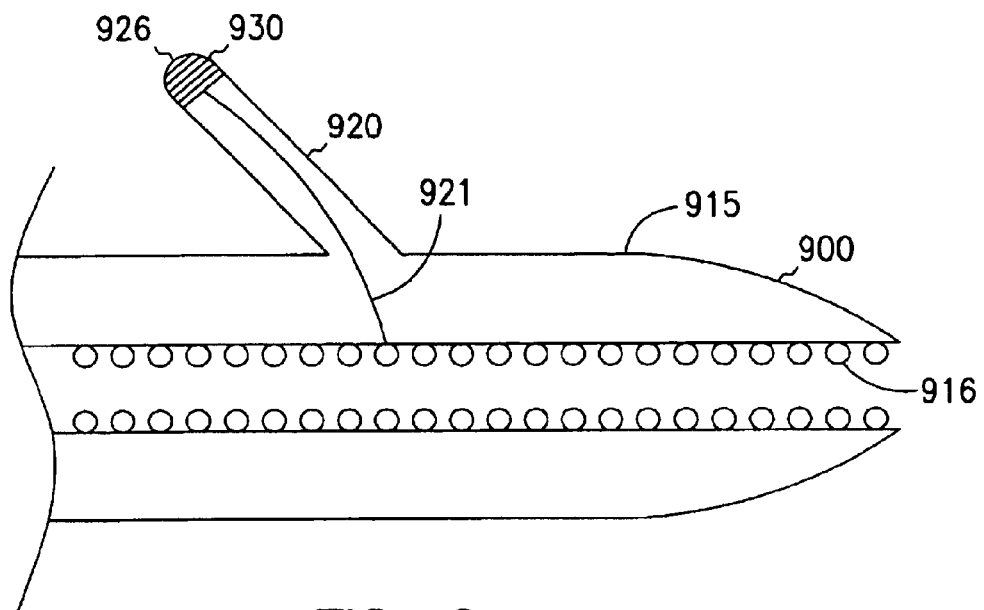
FIG. 9 is a cross-section of an electrode assembly constructed in accordance with one embodiment.

FIG. 9 illustrates another embodiment of a lead 900 with at least one conductive tine 920. The tine 920 is, in one embodiment, coupled with a lead body 915 and is electrically coupled with a conductor coil 916, as further discussed below. The tine 920 is adapted to send and receive electrical signals within a patient, such that the at least one conductive tine 920 serves as an electrode, or supplements the pacing or sensing of another electrode. In addition, the conductive tine 920 assists in fixating the lead 900 within a patient.

The tine 920, in one embodiment, comprises a slender projection which projects from the lead body 915. A conductive cap 930 is disposed on a distal end 926 of the tine 920. It should be noted, however, that the conductive cap 930 can be disposed on other portions of the tine 920. In one embodiment, the conductive cap 930 is coupled with the tine 920. Disposed within the tine 920 is a conductive element 921 formed of a conductive material, for example, a metal wire. Alternatively, in another embodiment, the conductive element 921 is formed of a flat wire or a foil.

The conductive element 921 is electrically coupled with a conductor coil 916 of the lead 900, for instance, by welding, crimping, or by conductive adhesive. In addition, the conductive element 921 is electrically coupled with the conductive cap 930, and forms the electrical connection between the conductive cap 930 and the conductor coil 916, which allows for the tine 920 to be conductive. The conductive cap 930 of the conductive tine 920 is adapted to contact tissue of a patient in which the lead 900 is implanted. In addition, the tine 920 assists in physically fixating the lead 900 within, for instance, a vein or artery.

Figure 10:
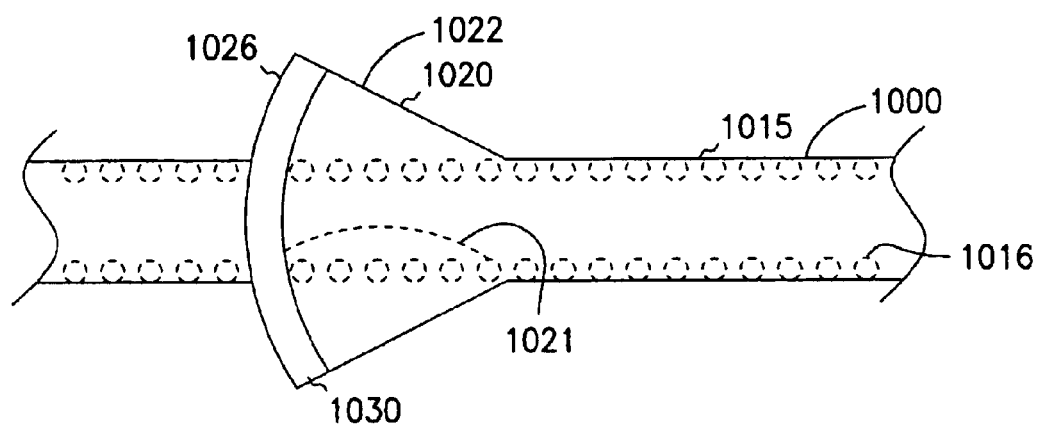
FIG. 10 is a side elevational view of an electrode assembly constructed in accordance with one embodiment.

Another embodiment of a lead 1000 is shown in FIG. 10, which illustrates a lead 1000 with at least one conductive fixation member 1020. The fixation member 1020 is, in one embodiment, coupled with a lead body 1015 and is electrically coupled with a conductor coil 1016, as further discussed below. The fixation member 1020 is adapted to send and receive electrical signals within a patient, serving as an electrode, or supplements the pacing or sensing of another electrode. In addition, the fixation member 1020 assists in fixating the lead 1000 within a patient.

The fixation member 1020, in one embodiment, comprises a cone 1022 which projects from the lead body 1015. The cone 1022 has a conical shape which is disposed about the lead body 1015. A conductive ring 1030 is disposed on a distal end 1026 of the fixation member 1020. It should be noted, however, that the conductive ring 1030 can be disposed on other portions of the fixation member 1020. In one embodiment, the conductive ring 1030 is coupled with the fixation member 1020. Disposed within the fixation member 1020 is a conductive element 1021 formed of a conductive material, for example, a metal wire.

The conductive element 1021 is electrically coupled with a conductor coil 1016, for instance, by welding or by conductive adhesive. In addition, the conductive element 1021 is electrically coupled with the conductive ring 1030, and forms the electrical connection between the conductive ring 1030 and the conductor coil 1016, which allows for the fixation member 1020 to be conductive. The conductive ring 1030 of the fixation member 1020 is adapted to contact tissue of a patient in which the lead 1000 is implanted, and allows for the conductive fixation member 1020 to serve as an electrode. In addition, the fixation member 1020 assists in physically fixating the lead 1000 within, for instance, a vein or artery of a patient.

Figure 11A:
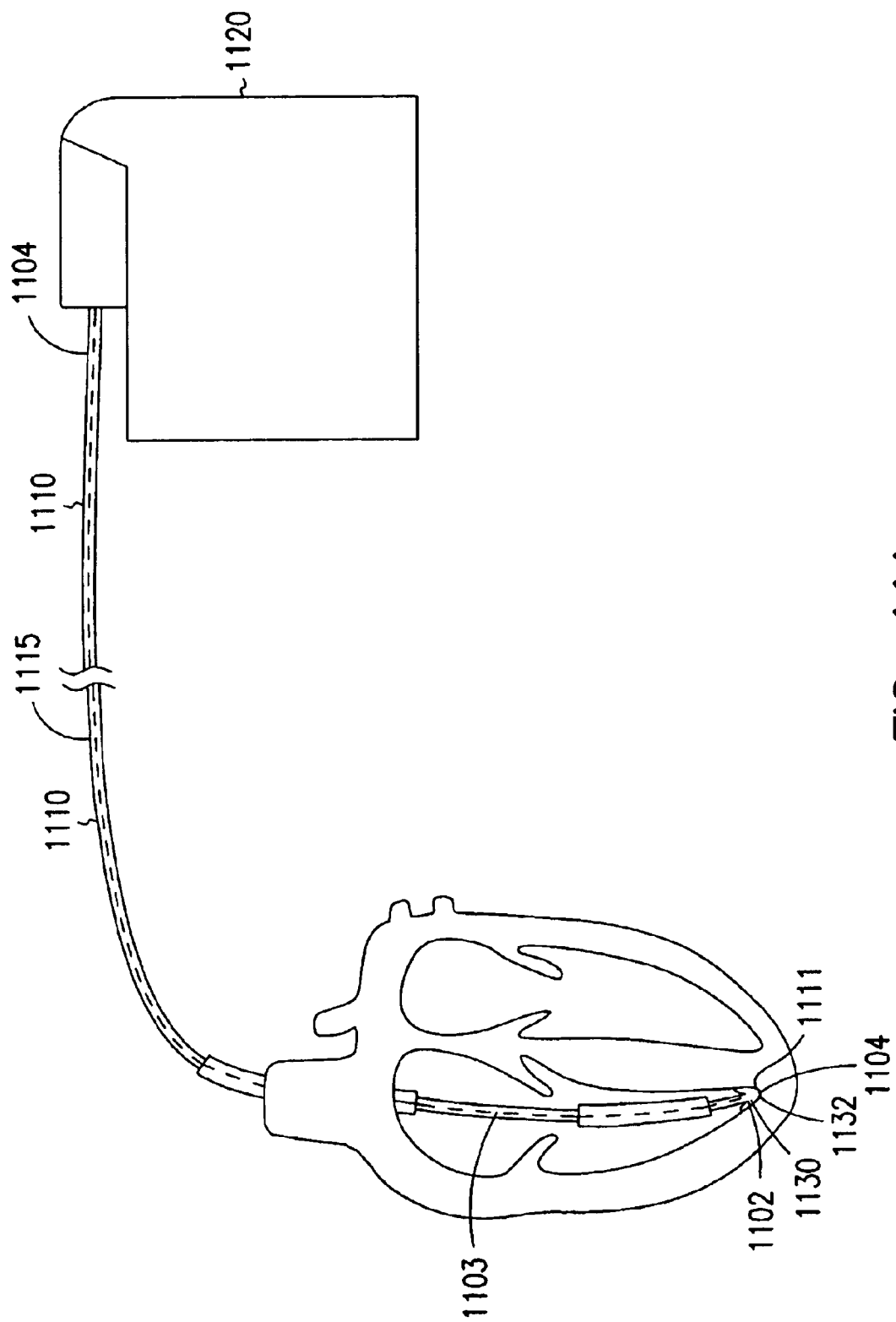
FIG. 11A illustrates a system for monitoring and stimulating the heart constructed in accordance with one embodiment.

FIG. 11A illustrates another embodiment of a lead 1100. The lead 1100 has a distal end 1102 which is implanted within a body, and a proximal end 1104. The proximal end 1104 has a connector terminal which electrically connects the various electrodes and conductors within the lead 1100 to a pulse generator 1120 and signal sensor. The pulse generator 1120 and signal sensor contains electronics to sense various electrical signals of a heart 1110 and also produce current pulses for delivery to the heart 1110.

The lead 1100 includes a lead body 1115, an elongate conductor 1116 contained within the lead body 1115, and at least one electrode assembly 1130. In one embodiment, the electrode assembly 1130 is disposed proximate to the distal end 1102 of the lead 1100. In another embodiment, the electrode assembly 1130 is disposed between the distal end 1102 and the proximal end 1104 of the lead 1100, at an intermediate portion 1103 of the lead 1100. The lead body 1115 is covered by a biocompatible insulating material. Silicone rubber or other insulating material are examples of materials which are used for covering the lead body 1115.

The elongate conductor 1116 defines a lumen 1217 therein (FIG. 12) and is adapted to receive a stiffening stylet that extends through the length of the lead 1100. The stylet stiffens the lead 1100, and can be manipulated to introduce an appropriate curvature to the lead 1100. The manipulation of the stylet facilitates the insertion of the lead 1100 into and through a vein and through an intracardiac valve to advance the distal end 1102 of the lead 1100 into, for example, a ventricle of the heart 1110. A stylet knob is coupled with the stylet for rotating the stylet, advancing the conductor into tissue of the heart, and for manipulating the lead 1100.

Figure 11B:
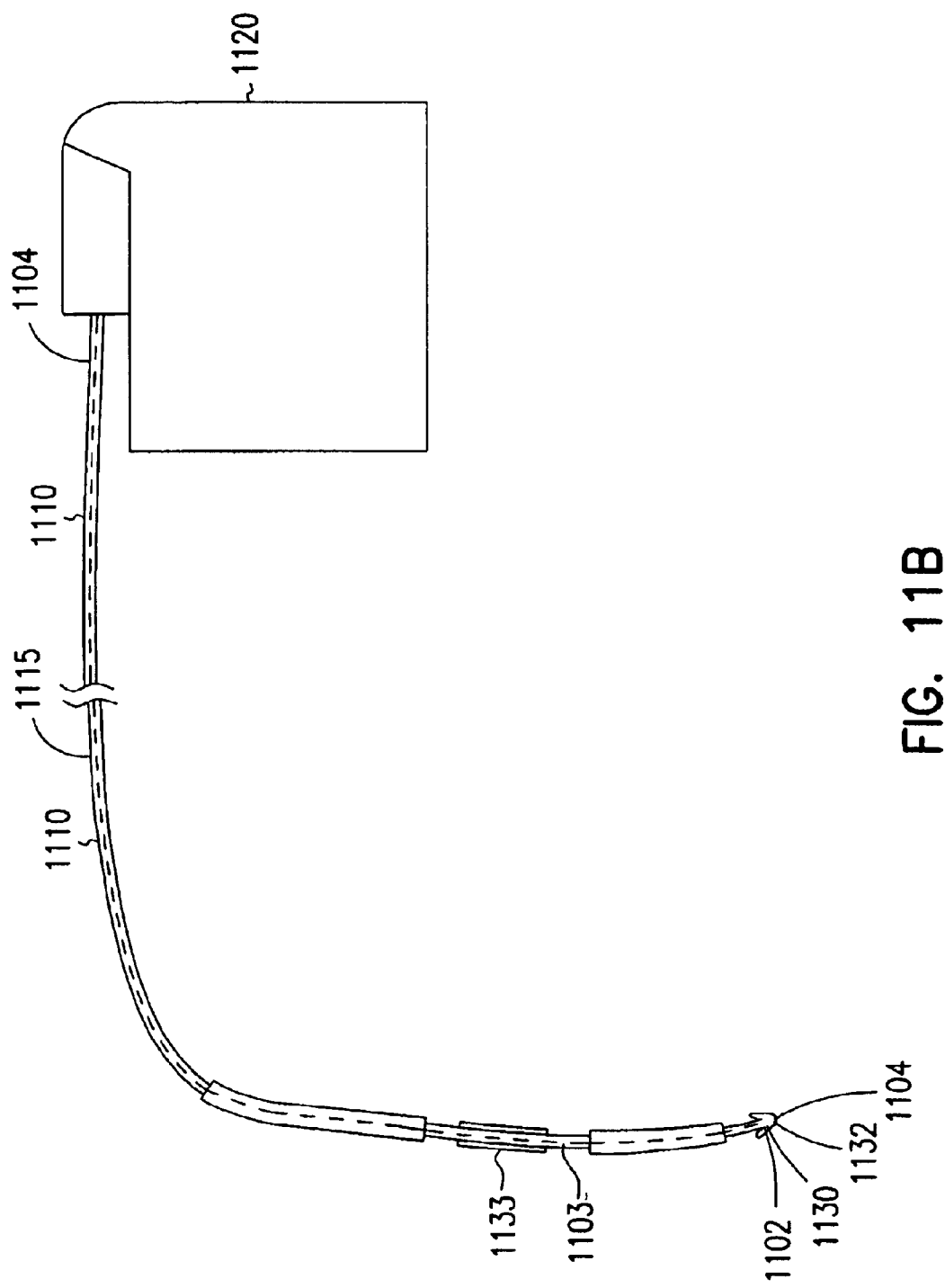
FIG. 11B illustrates a system for monitoring and stimulating the heart constructed in accordance with one embodiment.

The electrode assembly 1130 is adapted to be coupled with tissue, for example, within a heart 1110 or in a vein. In one embodiment, the electrode assembly 1130 includes a plurality of conductive tines 1120 and at least one defibrillation electrode 1132. In another embodiment, the defibrillation electrode 1132 extends to the distal end 1102 of the lead 1100, where the defibrillation electrode 1132 is disposed at a distal tip 1104 of the lead 1100. In yet another embodiment, as shown in FIG. 11B, the electrode assembly 1130 includes a plurality of defibrillation electrodes 1133.

Figure 12:
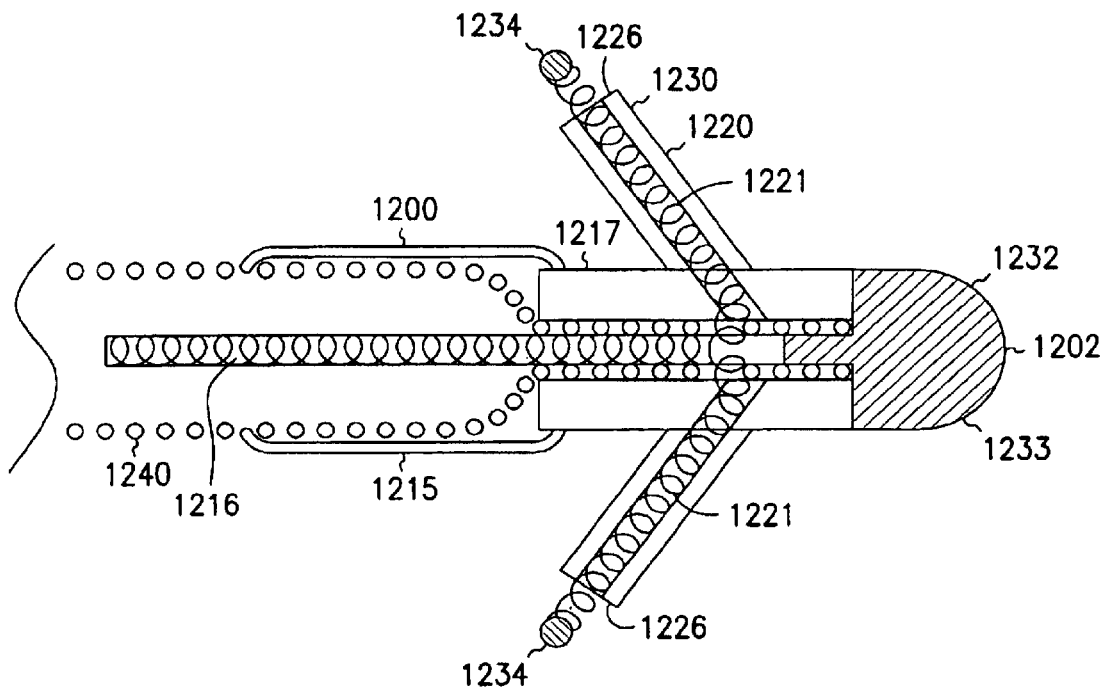
FIG. 12 is a cross-section of an electrode assembly constructed in accordance with one embodiment.

FIG. 12 illustrates another embodiment of an electrode assembly 1230, which includes at least one distal defibrillation electrode 1232. The distal defibrillation electrode 1232 is disposed at a distal tip 1202 of a lead 1200, where the defibrillation electrode 1232 is adapted to provide defibrillation shocks at the distal tip 1202 of the lead 1200. The electrode assembly 1230, in another embodiment, includes a proximal defibrillation electrode 1240. The proximal defibrillation electrode 1240 is electrically common with the distal defibrillation electrode 1232. In one embodiment, the tip 1233 of the defibrillation electrode 1232 has a smaller diameter than the proximal defibrillation electrode 1240, which accommodates pacing and sensing electrodes, discussed further below, without significantly increasing the profile of the lead 1200. Having the defibrillation electrode 1232 disposed at the distal tip 1202 allows for the defibrillation electrode 1232 to be positioned to the further possible extent within an apex 1111 (See FIG. 11A) of the heart 1110. It is believed that positioning the defibrillation electrode 1232 in this position assists in producing a favorable electric field distribution through the ventricular muscle, which lowers the shock strength requirement for defibrillation of the heart 1110.

Figure 13:
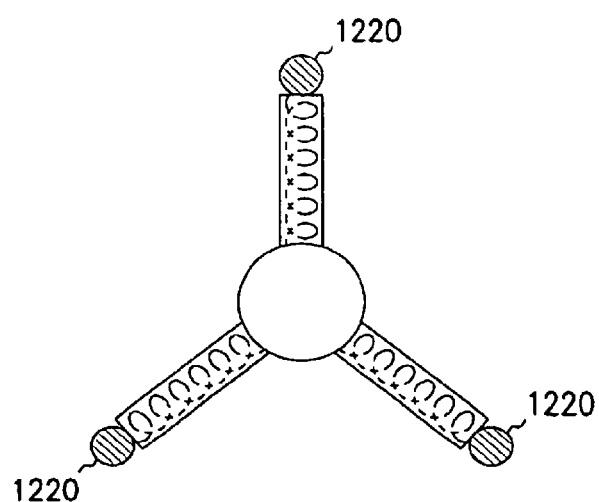
FIG. 13 is an end view of the electrode assembly shown in FIG. 12.

The electrode assembly 1230 further includes a plurality of conductive tines 1220. The conductive tines 1220, in one embodiment, comprise sensing and pacing electrodes. The tines 1220, in another embodiment, comprise slender projections which project away from the lead body 1215. In one embodiment, three conductive tines 1220 extend from the lead body 1215, as shown in FIG. 13. Insulation 1217 is disposed between the defibrillation electrode 1232 and the conductive tines 1220, for instance, silicone rubber, which prevents the electrode surface of the conductive tines 1220 from contacting the defibrillation electrode 1232. In one embodiment, a conductive member 1234, which serves as an electrode, is disposed on a distal tip 1226 of each of the tines 1220. In another embodiment, the conductive member 1234 is disposed on other portions of the tines 1220. In one embodiment, the conductive member 1234 is mechanically coupled with the tines 1220.

Disposed within each of the tines 1220 is a conductive element 1221 formed of a conductive material, for example, a metal wire. Alternatively, in another embodiment, the conductive element 1221 is formed of a flat wire or a foil. The conductive element 1221 is electrically coupled with a conductor coil 1216, for instance, by welding, crimping, or by conductive adhesive. In addition, the conductive element 1221 is electrically coupled with the conductive member 1234, and forms the electrical connection between the conductive member 1234 and the conductor coil 1216, which allows for the tines 1220 to be conductive. The conductive member 1234 of the conductive tines 1220 is adapted to contact tissue of a body in which the lead 1200 is implanted, and the member 1234 is adapted to sense and/or pace the tissue. In addition, the conductive tine 1220 assists in physically fixating the lead 1200 with tissue, for example within a vein or artery. It should be noted that variations to the conductive tines 1220, include, but are not limited to, the embodiments discussed above and below.

Figure 14A:
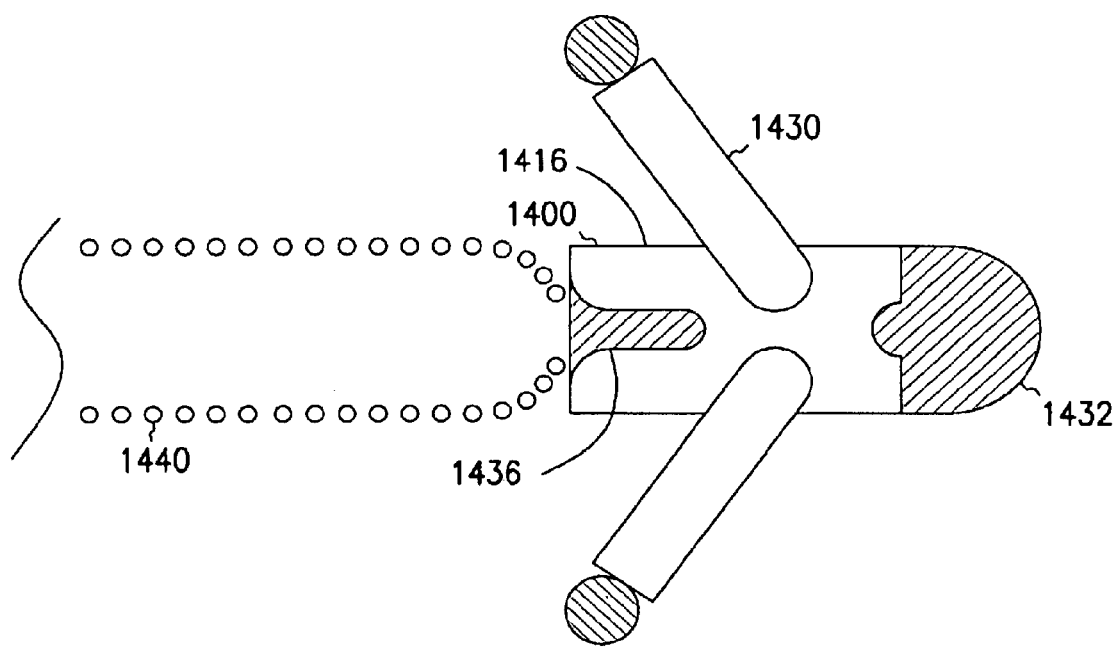
FIG. 14A is a cross-section of an electrode assembly constructed in accordance with one embodiment.
Figure 14B:
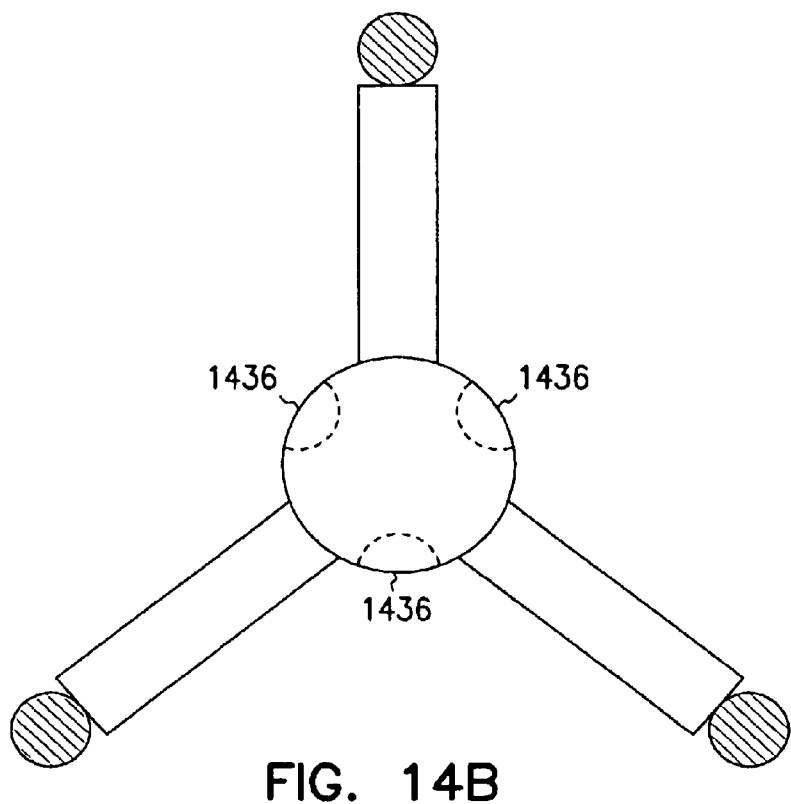
FIG. 14B is an end view of the electrode assembly shown in FIG. 14A.

FIGS. 14A and 14B illustrate another embodiment of an electrode assembly 1430 of a lead 1400. The electrode assembly 1430 is similar to that described above for FIGS. 12 and 13, and common elements are not repeated. The electrode assembly 1430 further includes a portion 1436 between a proximal defibrillation coil 1440 and a distal defibrillation coil 1432. The portion 1436 forms an electrical discharge surface for the defibrillation shock. Insulation 1416 is disposed between conductive tines 1420 and a lead body 1410 which covers the portion 1436 forming the electrical discharge surface for a defibrillation shock. In one embodiment, the shocking portion 1436 is exposed in three locations, 120 degrees apart, as shown in FIG. 14B.

Figure 15:
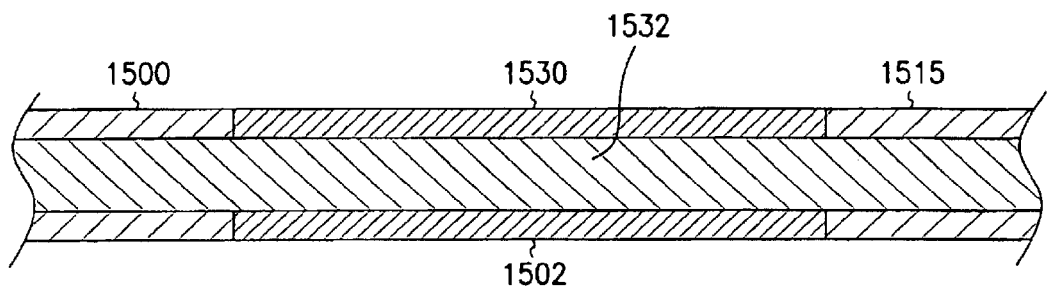
FIG. 15 is a cross-section of a portion of a lead constructed in accordance with one embodiment.

FIG. 15 illustrates an embodiment of a lead 1500 including an electrode assembly 1530. The electrode assembly 1530, in one embodiment, comprises at least one defibrillation electrode 1532. In another embodiment, the electrode assembly 1530 includes a pacing and/or sensing electrode, as discussed and shown above. The lead 1500 includes a lead body 1515, which is formed of a biocompatible insulating material, for example silicone rubber. A conductive material 1502 is disposed over the electrode assembly 1530, which facilitates the electrical connection between tissue which is to be stimulated and the electrode assembly 1530.

In one embodiment, the conductive material 1502 comprises conductive polymer, elastomer, or rubber which is molded over the electrode assembly 1530. The conductive material 1502, in another embodiment, comprises a sheath 1534 of conductive material. In another embodiment, the conductive material 1502 comprises, although is not limited to, any of the following: conductive polymers, rubbers, or elastomers like conductive silicone rubber and conductive thermoplastic elastomers like polyurethane elastomers, polyether-ester elastomers, and polyether-amide elastomers. In another embodiment, the conductive material 1502 comprises a combination of materials. In yet another embodiment, the electrode assembly 1530 is made from a conductive material including, but not limited to conductive polymers, rubbers, or elastomers like conductive silicone rubber and conductive thermoplastic elastomers like polyurethane elastomers, polyether-ester elastomers, and polyether-amide elastomers.

Figure 16A:
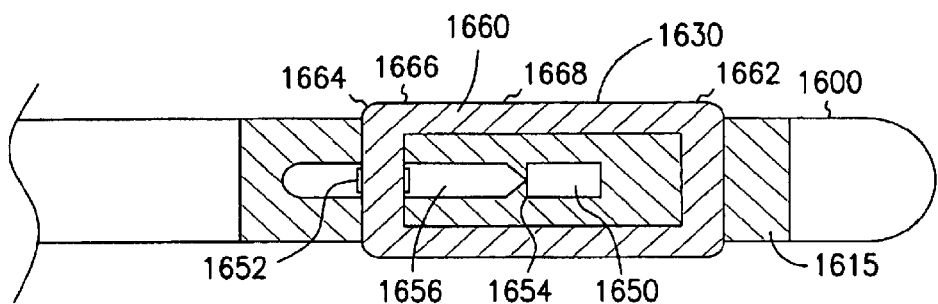
FIG. 16A is a cross-section of a portion of a lead constructed in accordance with one embodiment.
Figure 16B:
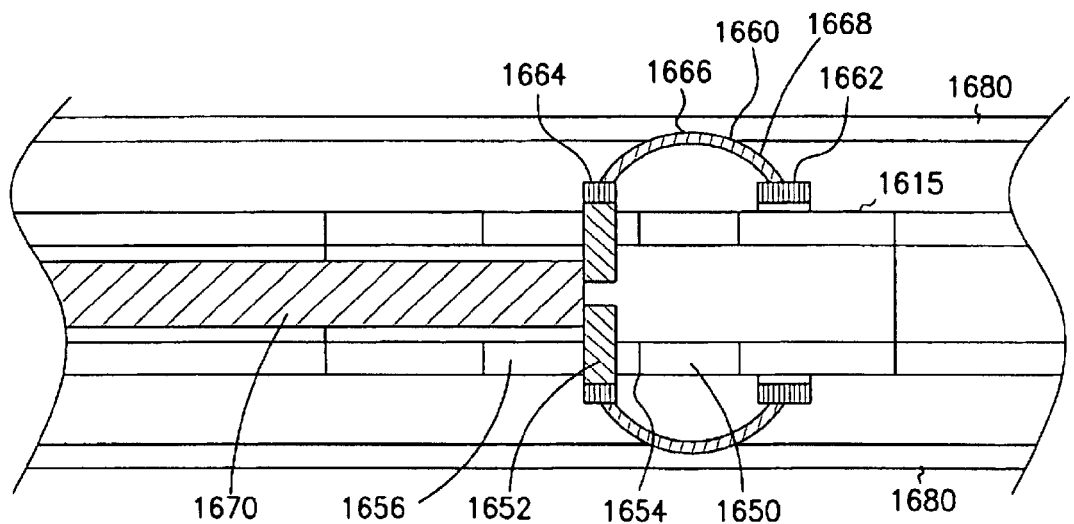
FIG. 16B is a cross-section of a portion of a lead constructed in accordance with one embodiment.

A lead 1600 of another embodiment is illustrated in FIGS. 16A and 16B. The lead 1600 includes an electrode assembly 1630 which has a conductive fixation feature 1660. The conductive fixation feature 1660 is adapted to send and/or receive signals from a heart. In addition, the conductive fixation feature 1660 fixates the lead 1600 within a body. In one embodiment, the conductive fixation feature 1660 is adapted to send and/or receive signals in conjunction with additional electrodes, as discussed above.

The conductive fixation feature 1660 extends from a first end 1662, which is fixed to a lead body 1615, to a second end 1664 which is movably coupled with the lead body 1615. An intermediate portion 1666 comprises a flexible conductive portion 1668. The flexible conductive portion 1668 is adapted to flex away from the lead body 1615 as the second end 1664 is moved toward the first end 1662, as shown in FIG. 16B. To deploy the conductive fixation feature 1660, a wire 1670 is disposed within the lead 1600 and pushed towards the second end 1664 of the conductive fixation feature 1660. In another embodiment, another deployment mechanism, such as a slide tube, is used to deploy the conductive fixation feature 1660 into a flexed position. As the second end 1664 is moved toward the first end 1662, the intermediate portion 1666 bows as it flexes away from the lead body 1615. As the conductive fixation feature 1660 is deployed, the overall diameter of the conductive fixation feature 1660 increases until it engages, for example, a vein 1680 to fixate the lead 1600 therein.

In one embodiment, the electrode assembly 1630 further includes a locking mechanism 1650 which maintains the conductive fixation feature 1660 in a flexed position. The locking mechanism 1650, in one embodiment, includes a slider 1652 which engages within an interference slot 1654. The slider 1652 is coupled with the second end 1664 of the conductive fixation feature 1660 and slides within a slot 1656 disposed within the lead 1600. The slider 1652 freely slides within the slot 1656 unless it is engaged by the interference slot 1654, which provides an interference fit between the slider 1652 and the interference slot 1654. Once the slider 1652 is engaged with the interference slot 1654, the intermediate portion 1666 of the conductive fixation feature 1660 flexes away from the lead body 1615 into the vein 1680 to fixate the lead 1600 therein.

Figure 17A:
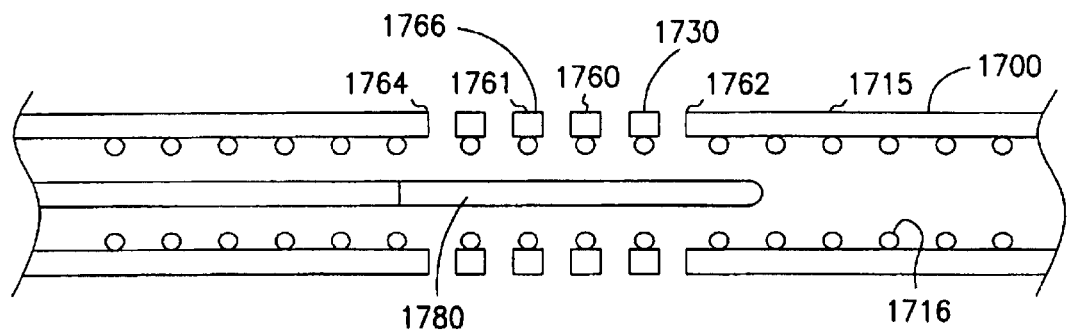
FIG. 17A is a cross-section of a portion of a lead constructed in accordance with one embodiment.
Figure 17B:
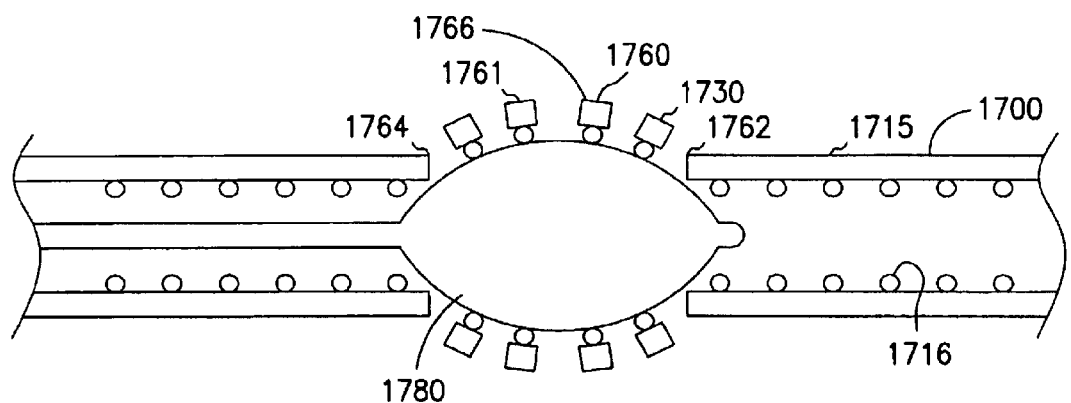
FIG. 17B is a cross-section of a portion of a lead constructed in accordance with one embodiment.

FIGS. 17A and 17B illustrate yet another embodiment of a lead 1700. The lead 1700 includes a lead body 1715 and an electrode assembly 1730 which has a conductive fixation feature 1760. The conductive fixation feature 1760 is adapted to send and/or receive signals from a heart. In addition, the conductive fixation feature 1760 fixates the lead 1700 within a body. The conductive fixation feature 1760 is electrically coupled with a conductor 1716 disposed within the lead body 1715. In one embodiment, the conductive fixation feature 1760 comprises a stent conductor 1761. In another embodiment, the conductive fixation feature 1760 is adapted to send and/or receive signals in conjunction with additional electrodes, as discussed above.

The conductive fixation feature 1760 extends from a first end 1762 to a second end 1764, and includes an intermediate portion 1766 therebetween. The intermediate portion 1766 comprises a flexible conductive portion 1768 which is adapted to flex away from the lead body 1715 when the conductive fixation feature 1760 is deployed, as shown in FIG. 17B. To deploy the conductive fixation feature 1760, a balloon catheter 1780 is disposed within the lead 1700. As the balloon catheter 1780 is expanded, as shown in FIG. 17B, the intermediate portion 1766 bows as it flexes away from the lead body 1715. The overall diameter of the conductive fixation feature 1760 increases until it engages a vein to fixate the lead 1700 therein.

Advantageously, the conductive tines aid in providing an implantable medical device which allows for fixation of a the medical device within tissue, such as a vein or artery. A further benefit is that the fixation feature includes an electrode which can sense or pace the tissue to which it is fixated. The conductive fixation feature also provides resistance to inadvertent dislodgment of the medical device from the patient.

It is believed that positioning the defibrillation electrode at the distal portion of the lead assists in producing a favorable electric field distribution through the ventricular muscle, which lowers the shock strength requirement for defibrillation. The combination of the defibrillating electrode and the pacing/sensing electrode disposed on conductive tines allows for the pacing/sensing electrodes to be disposed proximate to the distal end of the lead, yet are sufficiently spaced from the defibrillating electrode to avoid sensing problems following a shock from the defibrillation electrode.

It is to be understood that the above description is intended to be illustrative, and not restrictive. Although the use of the lead has been described for use in a cardiac pacing system, the lead could as well be applied to other types of body stimulating systems. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:

disposing a defibrillation electrode tip on a distal end of a lead body, the lead body extending from a proximal end to the distal end and having an intermediate portion therebetween;

coupling at least one conductive tine with the intermediate portion of the lead body;

positioning the defibrillation electrode tip within an apex of a ventricle of a heart and positioning the at least one conductive tine also within the ventricle;

coupling the lead body to a pulse generator;

delivering defibrillation shocks from the pulse generator via the defibrillation electrode tip; and pacing the heart with the at least one conductive tine.

2. The method as recited in claim 1, further comprising sensing the heart with the at least one conductive tine.

3. The method as recited in claim 1, further comprising disposing a conductive member on a distal tip of each conductive tine.

4. The method as recited in claim 1, further comprising coupling a conductive member to the at least one conductive tine.

5. A method comprising:

disposing a defibrillation electrode tip on a distal end of a lead body, the lead body extending from a proximal end to the distal end and having an intermediate portion therebetween;

coupling at least one conductive tine with the intermediate portion of the lead body;

positioning the defibrillation electrode tip within an apex of a ventricle of a heart and positioning the at least one conductive tine also within the ventricle;

coupling the lead body to a pulse generator;

delivering defibrillation shocks from the pulse generator via the defibrillation electrode tip; and sensing the heart with the at least one conductive tine.

6. A method comprising:

disposing a defibrillation electrode tip on a distal end of a lead body, the lead body extending from a proximal end to the distal end and having an intermediate portion therebetween;

coupling at least one conductive tine with the intermediate portion of the lead body;

providing insulation between the defibrillation electrode tip and the at least one conductive tine;

positioning the defibrillation electrode tip within an apex of a ventricle of a heart and positioning the at least one conductive tine also within the ventricle;

coupling the lead body to a pulse generator; and delivering defibrillation shocks from the pulse generator via the defibrillation electrode tip.

7. The method of claim 6, further including sensing or pacing with the conductive tine.

8. A method comprising:

providing a lead having a defibrillation electrode on a distal end of the lead and a conductive tine proximate the distal end of the lead;

positioning the defibrillation electrode at an apex of a ventricle of a heart such that the conductive tine is also within the ventricle;

coupling the lead body to a pulse generator;

delivering defibrillation shocks from the pulse generator via the defibrillation electrode; and pacing the heart with the conductive tine.

9. The method of claim 8, further comprising sensing the heart with the conductive tine.

10. A method comprising:

providing a lead having a defibrillation electrode on a distal end of the lead and a conductive tine proximate the distal end of the lead;

positioning the defibrillation electrode at an apex of a ventricle of a heart such that the conductive tine is also within the ventricle;

coupling the lead body to a pulse generator;

delivering defibrillation shocks from the pulse generator via the defibrillation electrode; and sensing the heart with the conductive tine.

11. The method of claim 10, further comprising disposing a conductive member on a distal tip of each conductive tine.

12. The method of claim 10, further comprising disposing a defibrillation coil at the intermediate portion of the lead body.

13. The method of claim 10, wherein providing a lead includes the conductive tine having a first end coupled with the lead body and a second end which extends away from the lead body.

14. The method of claim 10, wherein providing a lead includes the conductive tine being partially covered with non-conductive material.

15. The method of claim 10, wherein providing a lead includes coupling a conductive bead with the second end of the conductive tine.

16. The method of claim 15, wherein coupling a conductive bead includes welding the conductive bead to the conductive tine.

17. A method comprising:

providing a lead having a defibrillation electrode on a distal end of the lead and a conductive tine proximate the distal end of the lead;

providing insulation between the defibrillation electrode and the conductive tine;

positioning the defibrillation electrode at an apex of a ventricle of a heart such that the conductive tine is also within the ventricle;

coupling the lead body to a pulse generator; and delivering defibrillation shocks from the pulse generator via the defibrillation electrode.

* * * * *